(12) United States Patent
Neuberger (10) Patent No.: US 6,918,905 B2
(45) Date of Patent: Jul. 19, 2005

(54) MONOLITHIC IRRADIATION HANDPIECE

(75) Inventor: Wolfgang Neuberger, Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 78 days.

(21) Appl. No.: 10/103,261

(22) Filed: Mar. 21, 2002

(65) Prior Publication Data

US 2003/0181893 A1 Sep. 25, 2003

(51) Int. Cl.[7] .............................................. A61B 18/20
(52) U.S. Cl. ............................................ 606/9; 606/13
(58) Field of Search ................................ 606/9–13, 17; 607/88–90

(56) References Cited

U.S. PATENT DOCUMENTS

| | | | | |
|---|---|---|---|---|
| 3,865,113 A | * | 2/1975 | Sharon et al. ................. | 606/19 |
| 4,998,538 A | | 3/1991 | Charowsky et al. | |
| 5,364,390 A | * | 11/1994 | Taboada et al. ............... | 606/10 |
| 5,720,772 A | * | 2/1998 | Eckhouse ....................... | 606/9 |
| 5,728,041 A | | 3/1998 | Fowler, Jr. | |
| 6,228,074 B1 | * | 5/2001 | Almeida ......................... | 606/9 |
| 6,261,310 B1 | | 7/2001 | Neuberger et al. | |
| 6,595,986 B2 | * | 7/2003 | Almeida ......................... | 606/9 |

* cited by examiner

Primary Examiner—David M. Shay
(74) Attorney, Agent, or Firm—B J Associates; Bolesh J Skutnik; Thomas Ryan (57) ABSTRACT

A handpiece for topical application of electromagnetic radiation is disclosed, consisting of a single monolithic transparent block covered by a semitransparent coating on the faces of the block not directed toward a treatment site. The block and coating are transparent to visible radiation, allowing the user a direct view of the treatment site. At the same time, for the safety of the user and a patient, the monolithic block has a coating of radiation blocking or absorbing material to selectively prevent treatment radiation from harming a user or patient. In a preferred embodiment, an optical fiber or fiber bundle coupled to a suitable power source is directly molded into the monolithic block. This invention is useful for a broad variety of laser applications, including the treatment of dermatological diseases and paint removal. The simple monolithic structure allows the device to be portable and practical in open environments. Optionally, the handpiece may contain cooling mechanisms to alleviate overheating of the treated site in high power situations. Other embodiments contain further safeguards including sensors to provide feedback to the power source for more precise control of radiation and thus are available in preferred embodiments.

30 Claims, 6 Drawing Sheets

MONOLITHIC IRRADIATION HANDPIECE

BACKGROUND OF THE INVENTION

1. Field of the Invention

The present invention relates to the field of laser application, in particular to the treatment of dermatological diseases by the application of optical radiation and to selected methods in laser material processing such as restoring processes for buildings or paint removal.

2. Information Disclosure Statement

The scope of the present invention includes direct illumination, as for example in temperature treatments, and the combination of optical irradiation with suitable secondary substances and process management means. The invention provides a method to overcome the significant drawbacks of the state of the art concerning the application in the field of optical treatments in open environments.

Many applications, including direct ullumination and the use of optical irradiation in conjunction with other substances and processes, utilize optical laser treatments in open environments. Many of these applications employ coherent or partly coherent continuous or pulsed laser sources. These laser sources include fiber coupled light sources or beam sources that operate at wavelengths and intensity levels which can be particularly harmful to humans and other animals and thus require high standards of safety for the protection of the operator and the patient. The need for protection of the operators of applications utilizing optical irradiation is therefore a significant drawback to its use, considering the current state of the art.

In the state of the art, two techniques for ensuring the safety of laser processing are generally applied. The first technique is automation of the process, or control of the process with external devices, which generally includes steering elements such as computers and inspection devices such as CCD cameras. Automation enables one to enclose the process in a complete housing, thus isolating the process from outside users. Therefore, a laser application which is generally of class 4 can be reduced to a class 1 application. The significant disadvantage of this method is that it is only practical if an entire production environment can be planned, where the laser is included and the process conditions do not change. In medical environments, or in workshops, where the circumstances of the application are rapidly changing, a closed housing drastically reduces the versatility of the application.

In U.S. Pat. No. 5,728,041, Fowler, Jr. discloses a method and isolator for the filtering and removal of airborne contaminants produced in laser surgical or industrial procedures. The invention discloses a double chambered isolation chamber coupled with an air filtering and circulating unit. This invention is aimed at reducing the risk of infection during surgical procedures, as opposed to protecting the operator from radiation. In addition, this invention's usefulness may only be significant in implant procedures or procedures that weaken the patient's immune system. For the majority of procedures, air filtering systems currently used in hospitals suffice. This invention mandates that operators utilize sleeves through which arms can be inserted to perform the procedure. This is a cumbersome approach, as it may reduce the operator's flexibility, tactile feel, or vision when in use. Furthermore, the affected area must be fully enclosed in an inner chamber, which is then further enclosed by an outer chamber.

This patent, along with U.S. Pat. No. 4,998,538 (Medical Drape for Laser Surgery), attempts to create a more sterile environment by filtering or isolating airborne particles produced from laser surgical procedures. These inventions make no mention of radiation, nor do they claim any ability to protect an operator from potentially harmful electromagnetic radiation.

For procedures requiring flexibility, or where circumstances change regularly, a second technique is utilized. This second technique involves providing suitable personal safety equipment to the operator and all persons who must enter the environment in which the laser operates. This solution is not only very inconvenient, it also hinders process management and may limit the operator's performance of the process. Typical elements of personal safety equipment include protective eye-wear and protective clothing, which would be used, for example, during processes involving strong ultraviolet radiation. Protective glasses or masks hinder the vision of the operator, and may hinder a detailed inspection of the treatment site by the operator. In addition to protective personal equipment for the operator and others involved in the procedure, means are needed for securing the laser interaction area against unauthorized entrants.

U.S. Pat. No. 6,261,310 by Neuberger et al. offers another solution, describing a hand-held delivery device that attempts to incorporate the safety precautions of previous techniques into a single device. This invention includes a barrier incorporated into an applicator that encloses an area around the treatment site in the form of a hollow bell- or spherical shaped enclosure which is sealed to the skin using a deformable cushion. In order to achieve a vacuum, or for air purification, an additional enclosure must be used. The device itself is composed of a movable bell, which may prove complex in certain situations such as emergency procedures, or may require more maintenance if parts get worn and need to be replaced. Also, its hollow body and use of deformable cushions may render it too fragile for some industrial and nonsurgical uses. This invention also may not be suitable for non-coherent radiation emitted by a lamp or for light with a continuous spectrum.

Therefore, there exists a need for a safety device that allows an operator to employ procedures and applications utilizing optical irradiation without the need for creation of a closed environment or for protective clothing and personal gear for the operator. There is also a need for a safety device of sufficient durability and tactile precision that it may be used in all types of applications and situations. The present invention fills this need.

BRIEF SUMMARY OF THE INVENTION

It is an object of the present invention to provide an apparatus which combines functional safety means while maintaining visibility of a process or treatment area.

It is another object of the invention is to provide a flexible apparatus which can be operated with a large number of radiation sources.

It is a further object of the invention is to provide an apparatus whose imaging properties can be varied easily in order to adjust the irradiation properties to the treatment process.

It is yet another object of the invention to provide an apparatus which is capable of including means for secondary process aids.

It is a still further object of the invention to provide a means for electronic inspection of the process.

It is still another object of the present invention to provide an efficient control mechanism to obtain laser safety.

Briefly stated, this invention provides a handpiece for topical application of electromagnetic radiation, consisting of a single monolithic transparent block including a blocking means surrounding the faces of the block not directed toward a treatment site. The block and blocking means are transparent to visible radiation, allowing the user a direct view of the treatment site. The blocking means consists of a coating or layer of radiation blocking or absorbing material to selectively prevent process radiation from harming a user or patient. In a preferred embodiment, an optical fiber or fiber bundle coupled to a suitable power source is directly molded into the monolithic block. This invention is useful for a broad variety of laser applications, including the treatment of dermatological diseases and paint removal. The simple monolithic structure allows the device to be portable and practical in open environments. Optionally, the handpiece may contain cooling mechanisms to alleviate overheating of the treated site in high power situations. Other embodiments contain further safeguards including sensors to provide feedback to the power source for more precise control of radiation and thus are available in preferred embodiments.

The above, and other objects, features and advantages of the present invention will become apparent from the following description read in conjunction with the accompanying drawings, in which like reference numbers in different drawings designate the same elements.

DETAILED DESCRIPTION OF THE PREFERRED EMBODIMENTS

The present invention provides a monolithic handpiece for use in medicine and materials processing. The handpiece is described as monolithic in that it is cast as a single piece and, in a preferred embodiment, from a single material. Said handpiece is capable of irradiating a treatment site or process object with electromagnetic radiation ("process radiation"), produced by a beam source such as a laser in a preferred embodiment, while protecting operating personnel from said radiation and allowing an unfettered view and a detailed inspection of the treatment site.

The disclosed monolithic applicator provides a connection to a beam source preferably via an optical fiber. Said monolithic device may further provide an optical arrangement of refractive elements to image the radiation emitted by the fiber to the treatment site and is basically transparent to light at visible wavelengths. Since the treatment radiation is only partly absorbed at the treatment site surface, it is a feature of the applicator to provide radiation blocking means for protecting the operator and the patient by simultaneously confining the process radiation to its interior while allowing real-time unassisted inspection of the treatment site by the operator in order to control the treatment process. Thus, the present invention is a significant improvment to the treatment process since it makes the need of personal safety equipment for operator and patient obsolete and allows a simple yet accurate treatment process.

The present invention overcomes the mentioned deficiencies of the state of the art in a novel way. It combines ease of application with effective protection means while allowing detailed inspection of the treatment site. It is inexpensive and can be utilized for a large number of processes in various fields of medical applications and materials processing. This is achieved by creating a monolithic handpiece, or one cast as a single piece by one or more transparent materials. The radiation is delivered to the handpiece from the beam source via, for example, an optical fiber and can be varied according to the process requirements. Said fiber is fixed or integrated into the monolithic handpiece in such a manner that the output from the fiber end irradiates the treatment site. The incorporation of an optical fiber allows the use of a large plurality of laser beam sources, such as Q-switched or mode-locked solid state lasers of various wavelengths, diode lasers and gas lasers. The large number of applicable laser-beam sources allows the invention to be used for many different processes in a large variety of fields. Other means to form and direct process radiation other than fibers may also be incorporated in the handpiece, such as lenses, waveguides and fiber bundles. Any of these directing and forming means can be directly integrated with the block or be inserted into a cavity created within the block.

Further, the connection between the fiber and the monolithic handpiece is such that an inspection of the treatment site is principally possible. In order to protect the operator the handpiece provides a number of features as blocking means to confine the radiation within the monolithic handpiece volume other than through those faces directed to the treatment area. Such features include the use of suitable dielectric coatings and absorbing means on the hand-piece surface designed such that they absorb or reflect the process radiation, but are transparent at different wavelengths to preserve the ability to directly view the treatment site or process area.

There are additional advantages that stem from the monolithic nature of the disclosed invention. Because every component of the handpiece can be integrated into a solid block, including any lenses used, the handpiece allows the operator to be extremely precise and prevents slipping or possible leakage that could occur with a handpiece that utilizes movable components. Furthermore, a cooling device utilized in conjunction with this invention is more effective and efficient because the entire block is directly cooled, allowing the entire treatment surface to be consistently and easily cooled.

Through said optical fiber the radiation is delivered from the external beam source which may be positioned at a distance away from the treatment site. This allows the user to easily change the beam source for varying treatments. It further enables the field use of strong laser sources requiring large driving power. Field use is of significant interest in certain domains of materials processing, as for example in paint removal or in monument restoration. The device itself is lightweight and can be operated by a single person. To be used in high altitudes the mass of the optical fiber and the optional electrical wires must also to be taken into account, but the whole device will still be light enough for these operations. Another important aspect is the ability to enlarge the process facilities by combining the handpiece with several secondary process means. These include conventional aspiration lines to remove the process by-products, which are important since many optical processes generate toxic products. Further supply lines can be integrated to donate curative, therapeutic or otherwise process-enhancing substances such as liquids, powders and so on to the process site.

Since safety is an important issue in all laser applications, especially for those which can not be confined to an isolated housing, the handpiece presented can be equipped with active electronic elements which assure the proper use of the device. They are connected to the beam source and are capable of switching said source via a suitable interlock mechanism. To achieve an even higher degree of security, critical points may be controlled with a fast photo-diode, which is also connected to a processing unit which switches the beam source off if a certain critical radiation intensity at a predefined wavelength is detected by the photo-diode.

Figure 1:
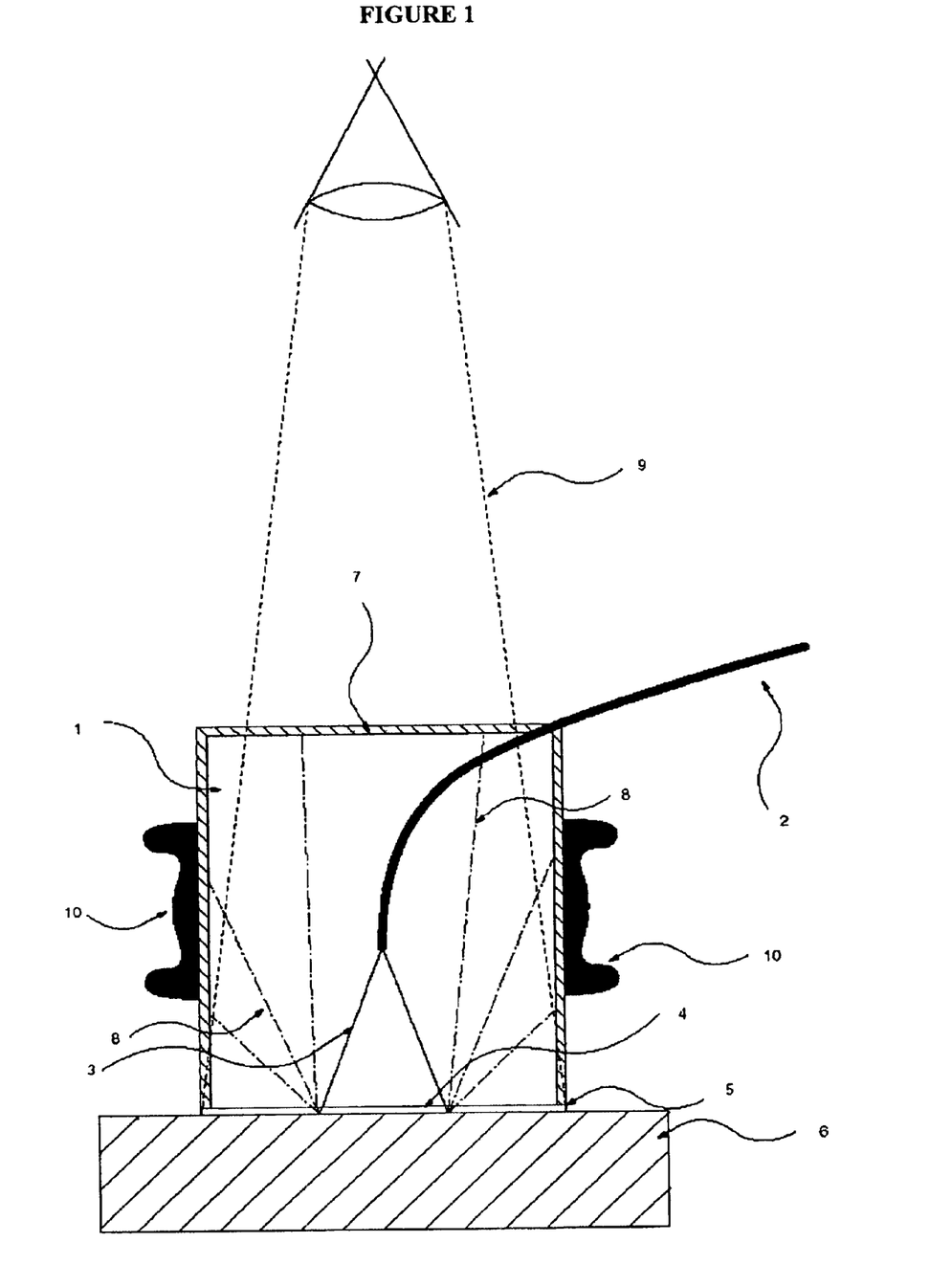
FIG. 1 depicts a basic embodiment of the handpiece.

FIG. 1 depicts the basic elements and one embodiment of the present invention. Optical fiber 2 is integrated into monolithic block 1. Block 1 consists of a homogeneous material which should fulfill a number of requirements, one of which is optical transparency for the process radiation. The material should also be durable, scratch resistant, and shock resistant to a certain degree. One suitable material is fused silica of optical quality, which can be molded and polished to achieve arbitrary shapes. Further, fiber integration is possible for the same reasons. Certain transparent polymers, such as PMMA can also be used to manufacture the monolithic element for the handpiece and to integrate the fiber therein. Other materials such as certain glass materials may also be used.

Electromagnetic radiation 3 emitted from the fiber end has a divergence angle which is given by three indexes of refraction: that of the fiber core, the fiber cladding and the monolithic block. The radiation can then propagate through the block to treatment site 4, where it initiates the process. The block is in contact or at a specific distance from treatment site 6. A specified distance from treatment site 6 can be achieved by the use of exchangeable spacers 5 between treatment site 6 and the handpiece. Spacers 5 can also be designed as a contact piece, which is fixed to block 1. To confine the radiation to the monolithic block, the exterior of the block is covered with protective coating 7. One typical feature of laser beam sources is that the radiation is emitted with an extremely narrow bandwidth. This makes the coating design simple and efficient. Taking into account the different angles at which scattered radiation hits the monolithic block surface, state of the art coatings can achieve degrees of reflection higher than 99.7% at the central wavelength. At this point the 0.3% of radiation passing through coating 7 is not enough to endanger the operator, and it also suffices for radiation which is not scattered diffusely, but reflected directly onto the coating. Dielectric coating 7 shows the targeted reflective behavior only in certain wavelengths, allowing other wavelength ranges to freely pass through. Light at this wavelength is thus predefined for inspection purposes. The small amount of reflected primary radiation 8 hits coated surfaces 7 but cannot freely pass through it, and is thus multiply reflected and finally absorbed in small and thus harmless amounts on the treatment site 6 or in monolithic block 1 itself. On the other hand, observation wavelength 9 freely passes through all of the coatings, allowing the user to see the treatment sight through the block.

In a preferred embodiment instead of using dielectric coatings protective surface 7 is made of an absorbing layer or a combination of an absorbing and reflecting layer. The absorbing layer contains additives, preferably ions, which strongly absorb the wavelength of the process radiation. Hence, reflection from the dielectric coating on the outer side of the monolithic block is absorbed directly, instead of being multiply reflected and finally absorbed.

The operator holds the handpiece with means for maneuvering, in this case, in the form of handles 10 which are fixed such that the view of the treatment site is not hindered and there exists a detailed control over the handpiece.

In many cases the optical radiation needed for the treatment process is not delivered by a laser beam source, such as in treatments using large area irradiation with ultraviolet radiation. For large areas the advantages of lasers are less significant compared to instances where small foci and high intensities are needed. For area illumination, fibers with small core sizes (a few millimeters) can be used in bundles. Radiation generated by a suitable lamp can be coupled into said bundles. Lamp-generated light is of course noncoherent and usually has a larger bandwidth than laser light. However, especially for ultraviolet application, excimer lamps are used and these may provide a single line at a certain wavelength. One example is light generated by xenon chloride at 308 nm. In most cases lamps have a continuous or at least quasi-continuous spectrum. Therefore the coatings must be of a high quality degree concerning the protection bandwidth, but since lamp light is of much lower intensity than laser radiation the requirements on the degree of reflection become smaller. Hence a suitable protection incorporated as a multi-coating structure can be found for any kind of process radiation.

At higher radiation powers, the radiation confined to the handpiece creates a temperature increase in the handpiece itself. There is also an even greater increase in the treatment site temperature, since its absorption properties are significantly stronger than those of the monolithic block. This heating effect may be counterproductive for many processes or treatments. A cooling device in the handpiece can be utilized to counteract this effect. The exterior of the handpiece can be cooled by simple solid state air cooling methods involving thermoelectric elements in the handpiece. The cooling of the treatment site is another significant advantage of the monolithic design. Because the block is in direct contact with the treatment site over a relatively large area, cooling the block can effectively and easily cool the treatment site, thus making the treatment safer and more comfortable for the patient by avoiding the negative side effects which may arise from high treatment temperatures. Needless to say, treatments which are based on heating or overheating the treatment site may still be performed. To cool the treatment site more efficiently, an active cooling method applying liquids, preferably water, can be included. This embodiment is described in more detail below.

Radiation other than the process radiation can be delivered through the fiber. A second light source, preferably a diode laser at a wavelength different from the process wavelength, can be coupled into fiber 2. The intensity of this beam source is low, as it is only used for aiming the primary process beam. The wavelength is such that it can pass through the dichroic coatings which confine the process radiation to the interior of block 1. If the aiming beam is coupled through the fiber, it will follow the same basic path as the process radiation and thus can be used to align the handpiece accurately to the treatment site. Another means for accurately positioning the handpiece is the use of a graticule, also known as a reticle, which is essentially a set of crosshairs. The reticle can be placed in the optical path or integrated, possibly by engraving, into the bottom of the monolithic handpiece and aligned with the process beam path to allow an exact alignment of the handpiece.

Figure 2:
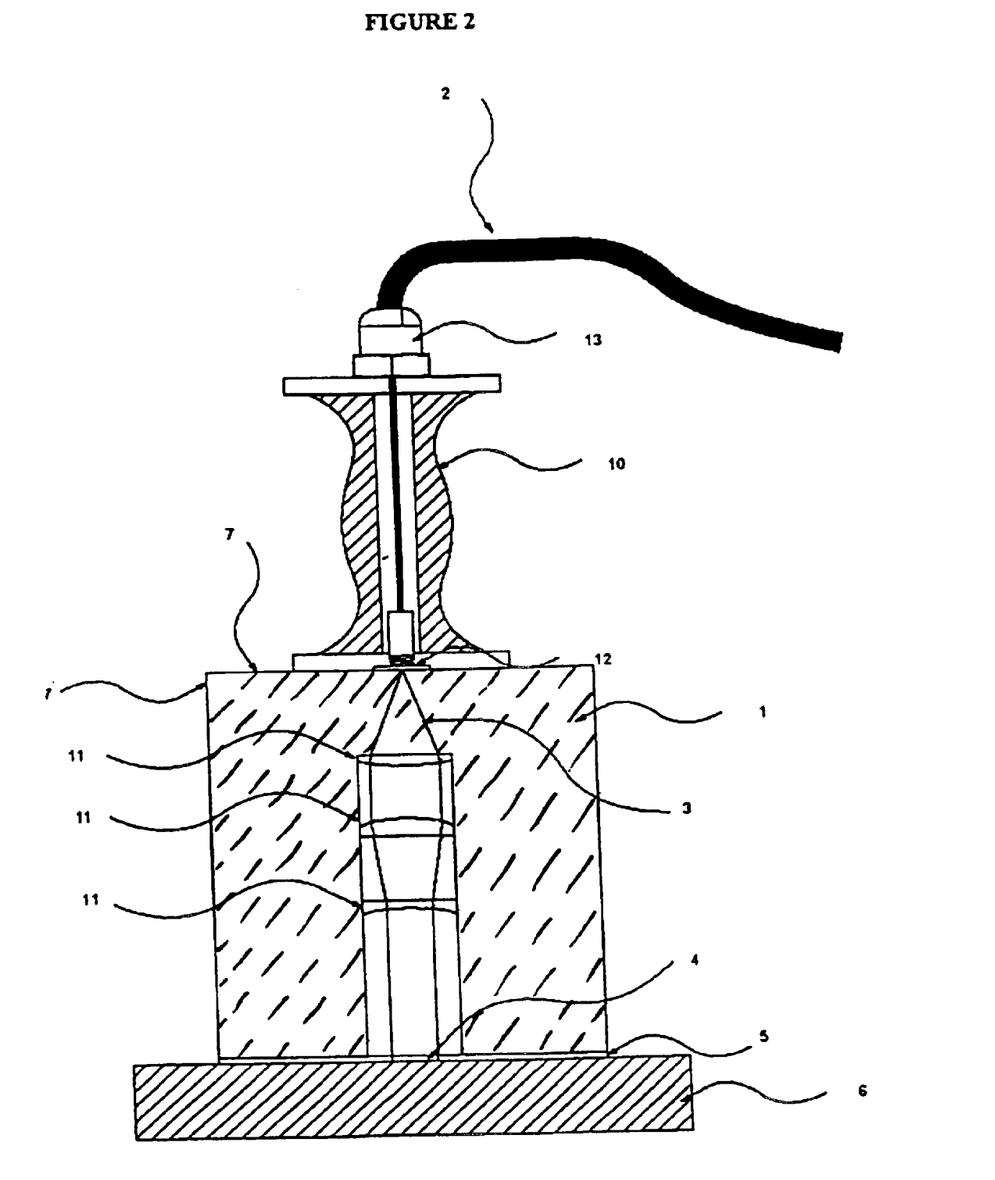
FIG. 2 illustrates the handpiece including a variable optical system for adjusting radiation intensity.

FIG. 2 illustrates another embodiment of the present invention. This embodiment shares monolithic block 1 and fiber 2 with the basic system in FIG. 1. Handle 10 is in alternative position in this embodiment. Handle 10 is fixed on the top of block 1, and fiber 2 travels through handle 10 to affixing means 13, which is used as means for coupling radiation from a source to fiber 2, on block 1. Affixing means 13 may be embodied as an SMA Connector, which is very popular as a connector for optical fibers. Additionally, electrical wires and even supply lines may be included with the fiber in a central duct and connected to the handle. Controls such as a switch and a safety means are also connected to handle 10. The system described in FIG. 2 is thus a modular system. The fiber and the handpiece may be disconnected completely, as opposed to the embodiment illustrated in FIG. 1. Hence, different fibers for different kinds of radiation may be utilized with the same handpiece. It is also possible to to use fibers with different properties, such as fibers with different numerical apertures or varying core diameters, with the same handpiece. In order to maintain the outstanding security measures it is still necessary to coat block 1 with suitable dielectric coatings 7. In order to operate the handpiece with more than one kind of radiation, providing in particular more than a single wavelength, coating 7 must be carefully designed to match all requirements.

The treatment site is still visible in this embodiment. As opposed to the embodiment illustrated in FIG. 1, where the inspection is a top view, the inspection in this embodiment is a side view of treatment site 6.

Another feature of the embodiment depicted in FIG. 2 is the ability to include and interchange different optical elements. A number of lenses 11 are included in the optical path of the radiation emitted by the optical fiber. A cylindrical cavity is drilled or directly molded into the monolithic block. This cavity need not be cylindrical, but such a shape is of advantage in the manufacturing process. Applying the more advanced method of directly casting the monolithic block and cooling it down, the variety of possible shapes and cavities is not limited. Maneuvering means can be the block itself, instead of handle 10, if the block is shaped appropriately.

Lenses 11 can be inserted into the cavity and easily fixed by mechanical means. This enables the user to shape radiation 3 into a number of possible forms. In particular, it is possible to generate spot sizes limited by the physical properties of the fibers and lenses. Further, line shapes can be formed by the application of cylindrical lenses and images of high complexity can be formed with apertures, diffractive optics and imaging means available in the state of the art. Contact cooling available in FIG. 1 would be restricted to the monolithic part, as there would be no contact with the treatment site in the area of the cylindrical cavity. However, as mentioned above, cooling of the entire treatment area can be realized by fixing contact element 5 to block 1. Channels for the liquids used to cool the treatment site are integrated into contact element 5. Further, contact element 5 is necessarily transparent to visible radiation for inspection purposes and to the specific process wavelength. Suitable materials for contact element 5 include various kinds of glasses, fused silica or durable polymers. Additional coatings on contact element 5 may reduce reflection losses from the surfaces and thus enhance the performance of the element. The channels needed for the liquid cooling can be manufactured into said element by various methods. For example, the structure, including the cooling channels may be manufactured directly by a casting process. An example and a detailed description is given with FIG. 4.

Figure 3:
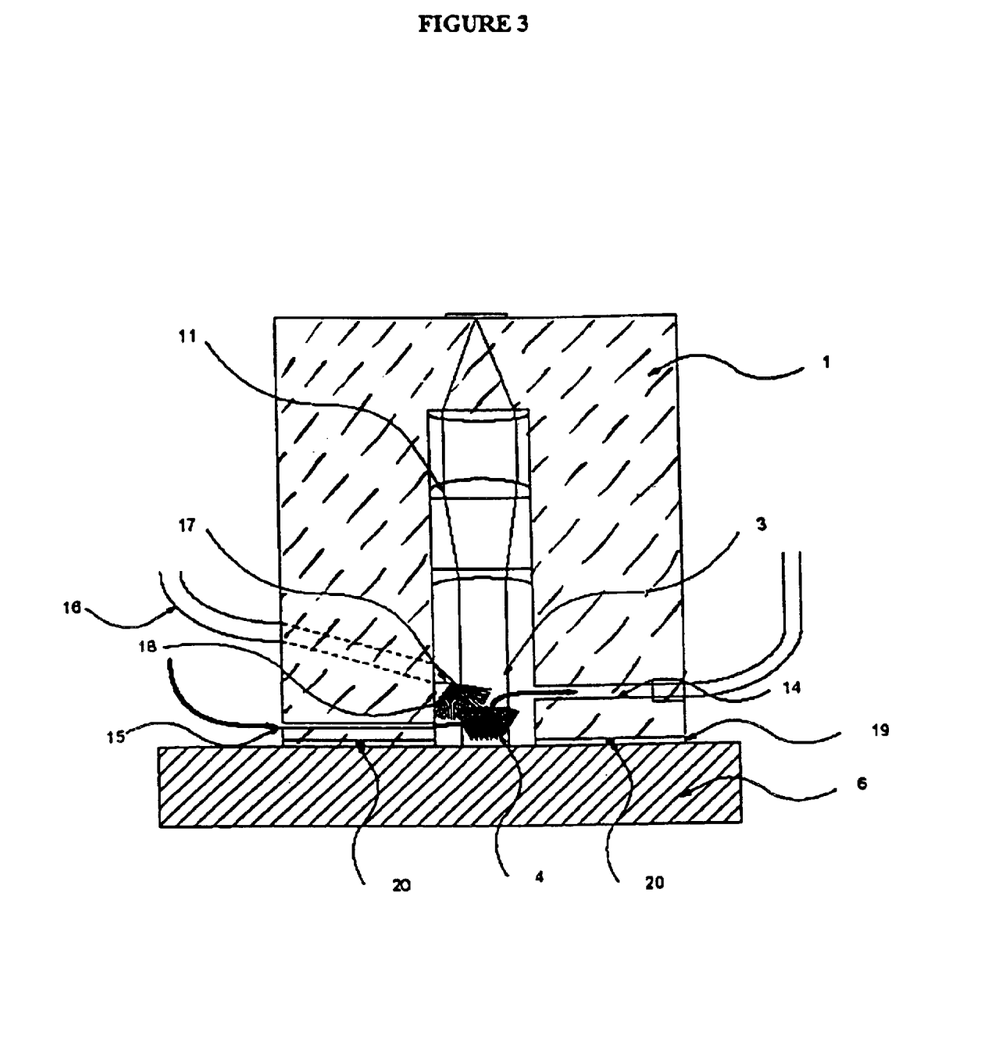
FIG. 3 shows a variation of the invention including a vacuum- and a supply line to deliver therapeutic or process-enhancing substances to the treatment area.

FIG. 3 shows the inclusion of several secondary processes to the monolithic handpiece. Two important additions are aspiration lines and supply lines for the inclusion of secondary process materials and therapeutic substances. Both methods are particularly useful for materials processing such as paint removal or restoration and also for medical applications. As an example, said elements are included into the modular incorporation described in detail above and illustrated in FIG. 2. In particular, the cavity between block 1 and treatment site 6 is modified as compared to the elements from FIG. 2. Here, contact plate 5, which is already optional, is omitted. Therefore, the process radiation is directly absorbed into the treatment site. Aspiration line 14 is incorporated into the monolithic block and connected to a conventional aspiration device such as a vacuum pump. An aspiration apparatus is especially useful for materials processing, but also useful for medical treatments that produce particles or smoke. This leads to debris on the lenses and resulting performance degeneration of the optical system in general, as well as absorption of the processing radiation by the particles themselves. These two effects produce a temperature increase of the monolithic block and the treatment site and other undesired side-effects. Aspiration line 14 provides a permanent flow of air along the treatment site to remove particles and avoid the above effects. The air needed can be aspirated through channels at bottom plate 19 of monolithic block 1 or through channels 15 included in block 1 itself. Another use for such a vacuum line is the creation of a low pressure atmosphere, in particular a concrete evacuation, in the treatment chamber. This can be achieved if o-ring gasket 20 is placed between treatment site 6 and block 1. Once the evacuation is started, the block itself is pressed onto the processing site. This permits the exclusion of atmospheric gases, such as Nitrogen or oxygen, which can be counterproductive for a number of processes. Alternatively, the chamber can be evacuated first and then be filled with a process atmosphere that has a predefined composition.

Supply lines 16 can be implemented for the addition of of secondary process and therapeutic liquids and gases to the process. These additions can range from liquids which may be a simple cooling means to medical additions like PDT drugs. The process additions are pressed through line 16 and through exchangeable directional means 17. Direction means 17 may, for example, consist of a nozzle and serve as an evaporation means for the supply substance. Means 17 may also be a simple aperture without any specialized effects. The substance is directed towards the treatment site where it serves for cooling or is excited by the radiation so that a therapeutic process is initiated. The permanent flow through the chamber caused by the vacuum line 14 can be established such that the supply substance, which may have already reacted or is heated, for example, can be aspirated and new fluid or other supply can enter the treatment site.

As an alternative to a central supply line, non-central supply lines can be integrated in block 1. For example, these lines may be incorporated as micro-channels within block 1 or in the bottom surface of block 1. Through these micro-channels, the fluid supply can be incorporated in a very homogeneous way without the need for an evaporation means such as means 17. The integration of micro-channels in the bottom surface of block 1 can be easily accomplished. One suitable method would consist of generating a mask with the desired structure and etching the channels into the glass. Another method to achieve this would be the application of short pulsed lasers in the nano-, pico- or femtosecond region. Of course, channels can already be included in the bulk manufacturing process.

Figure 4:
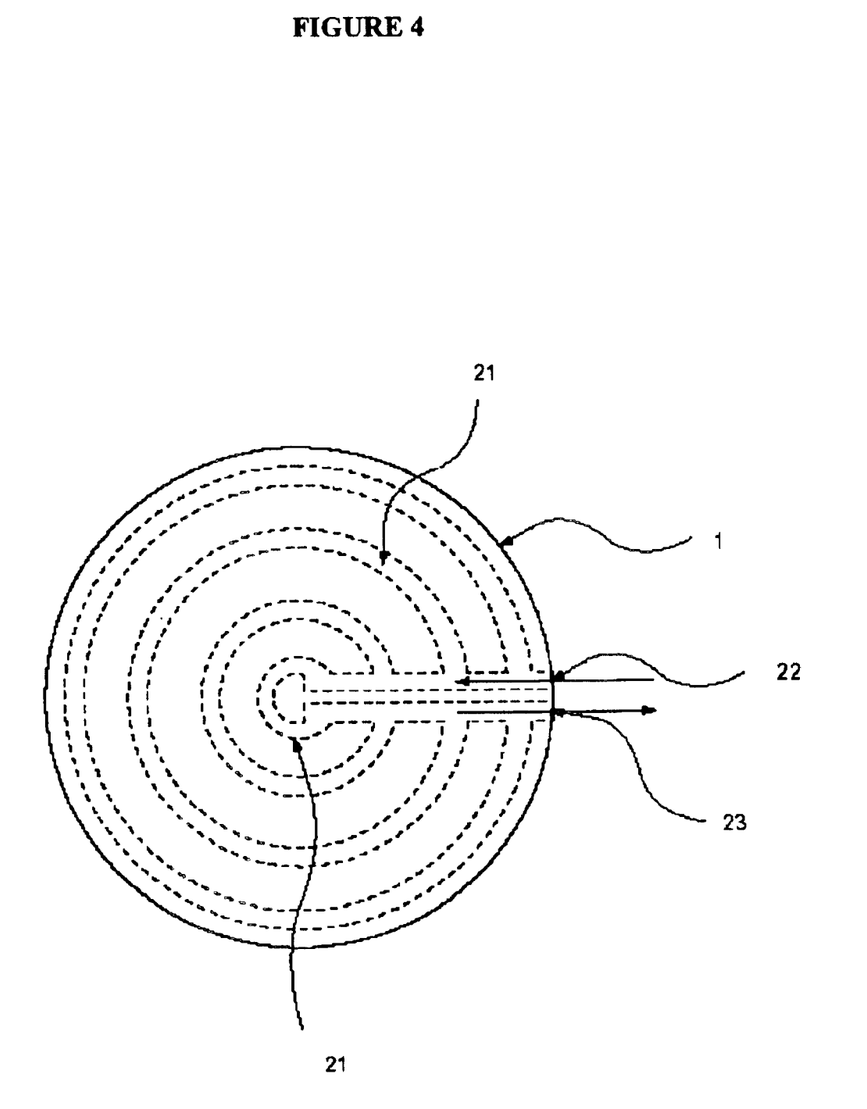
FIG. 4 illustrates an embodiment incorporating channels for cooling or heating the treatment site.

A design example of cooling channels for the handpiece is illustrated in FIG. 4. A different cooling principle is embodied herein, which is especially useful for medical treatments of the skin. FIG. 4 shows the bottom of the monolithic handpiece 1, for which a cylindrical basic shape is chosen as an example. Not shown in FIG. 4 are the optional cavity and fiber connectors. A net of cooling channels 21 are integrated into the bottom of the monolithic handpiece itself or, alternatively, into a suitable bottom plate which is fixed to monolithic handpiece 1. These cooling channels are isolated within the block or plate, so that a cooling fluid is not in contact with the treatment site. Monolithic handpiece 1 is in contact with the treatment site. Heat generated at the treatment site can be dissipated primarily by the monolithic block itself, which has a certain heat capacity and thus allows a heat flow to its interior. To improve heat transfer to the block, the use of a thermally conductive paste as an interface is possible in order to increase the surface in contact with monolithic block. Said paste can fulfill several functions and may also serve several treatment purposes. Some treatments such as PDT or hair removal require the use of a secondary treatment drug. Cooling channels 21 keep the bottom of the monolithic block at a constant temperature, since the cooling fluid circulates through cooling channels 21 and thus removes generated heat from the surface. The cooling fluid can have a large heat capacity, so the temperature difference between the cooling fluid 22 entering the cooling channels and the cooling fluid 23 leaving them again can be neglected. The cooling channels can be manufactured in a more or less dense network. As mentioned before, methods exist that allow the generation of cooling channels whose diameter is several micrometers. This has an influence on the cooling efficiency and on the cooling homogeneity. In general a more dense network of smaller cooling channels leads to an increased efficiency and homogeneity. However, flow-rates of the cooling means are correspondingly decreased. In addition the manufacturing of small channels is more difficult, hence from the special application one must decide how to design the optimal cooling method. The cooling means itself must fulfill some additional requirements. Since it is a generally advantageous feature of the invention that the treatment process can be observed directly by the operator, the method used to cool the bottom must be such that it is transparent to the observation wavelength. Further it must be transparent to the process wavelength, at least in those parts where the process radiation crosses the cooling surface. The most obvious choice for a cooling fluid is water, but others, such as glycerine or gaseous nitrogen are also possible. From an optical point of view, a cooling fluid that has the same index of refraction as block 1 or the bottom plate is advantageous so that no optical distortions can occur. For the same reason, the design of the cooling channels must be accomplished to achieve a laminar flow of the cooling fluid. If the flow is turbulent, large pressure differences occur in the turbulent regions causing fluctuations of the refraction index, which can result in distortion of the optical image.

As indicated above, laser applications are generally accompanied by a number of safety problems which strongly limit their use. Generally these problems are solved by housing the laser treatment system and inspecting it with passive means such as CCD Cameras and coated windows. The beam source is then controlled by automated processes such as n-axis stages or robotics. In ambulant medicine and outdoor materials processing, personal safety equipment is required and measures to prevent persons from entering the region wherein laser radiation can occur must be chosen.

Figure 5:
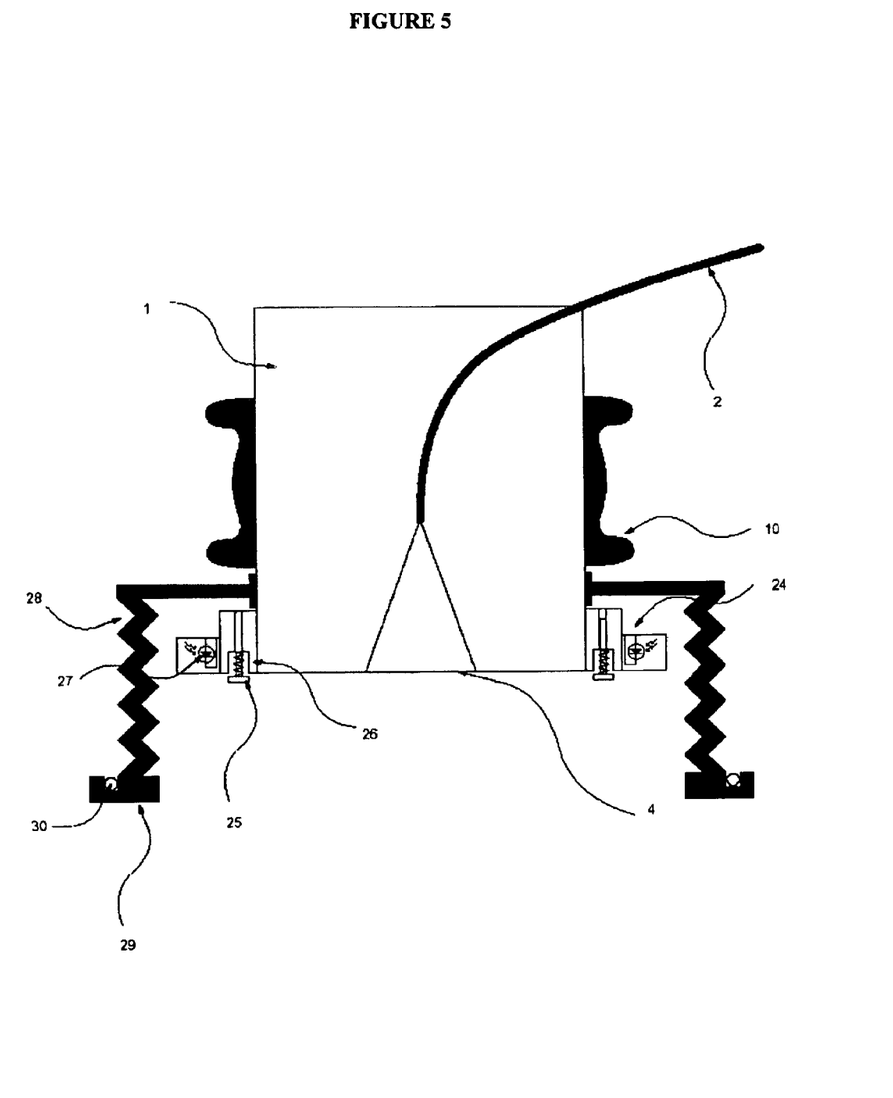
FIG. 5 illustrates a simple contact security device included in the handpiece.

As mentioned before, the monolithic handpiece solves several of these problems by implementing suitable optical coatings or absorbing materials which prevent the radiation from leaving the monolithic block expect to the treatment area. In FIG. 5, a vertical cross section of the monolithic handpiece including additional means for increasing the safety of the handpiece is shown. One such means is an interlock system including an electrical contact switch system and a means to prevent radiation from being emitted through the handpiece. Around the circumference of the monolithic block a number of electrical contacts 24 is positioned. Contacts 24 are connected to an interlock mechanism. The light source can only be switched on, and thus irradiation of the treatment site can only be started, if all contacts 24 are closed. The contacts are designed in such a way so that they will not close, and hence the light source cannot be activated, unless there is a seal between surface 29 and the treatment surface. The use of more than one contact of this type further ensures that the monolithic block is in contact with the treatment site at its whole surface. Alternatively, a contact system with a ring shape can be included in the bottom plate and along this ring several contact points can be positioned in order to guarantee complete contact. The use of electrical contacts of this type is simple. Stamp 25 is prepositioned with spring 26, and the initial position of a stamp is such that the electrical switch incorporated in the contact is open. If monolithic block 1 is pressed against the treatment site, stamp 25 moves up and closes the contact. If the handpiece is removed from the treatment site accidentally, the spring presses the stamp back into the open position and the light source is switched off.

Additionally, photo-diodes 27 connected to the interlock security system can be fixed at the contact points 24 or elsewhere on the monolithic block. If radiation passes from the treatment site, the photo-diodes produce a certain diode current which is detected by the light source driving means. Therefore photo-diodes 27 must be carefully calibrated to the treatment or process wavelength. Normal illumination causes the general photocurrent, but if process light is detected, the current is much higher. The relative sensitivity of photodiodes 27 to the process radiation can be enhanced by using dielectric coatings, through which only radiation with the process wavelength can pass.

An additional security element is depicted in FIG. 5. Motor bellow 28 is positioned around the circumference of the monolithic handpiece. It consists of a durable yet flexible material that is not transparent to light at the process wavelength. Motor bellow 28, by design, is positioned on the handpiece so that it comes in contact with the treatment site before block 1 or stamp 25 comes in contact with the treatment site. Because of the flexibility of bellow 28, the handpiece can be moved towards the treatment site and be positioned thereon without motor bellow 28 leaving the surface. It is preferably incorporated with the same cylindrical design as the monolithic handpiece. At the bottom of motor bellow 28, solid foot 30 and ring 29 stabilize the contact surface. Motor bellow 28 is preferably completely non-transparent, but the user would still be able to see the treatment site. This is an additional safeguard, contemplated for a situation in which the handpiece is accidentally moved from the treatment site and the interlock mechanism does not react sufficiently quickly.

Figure 6:
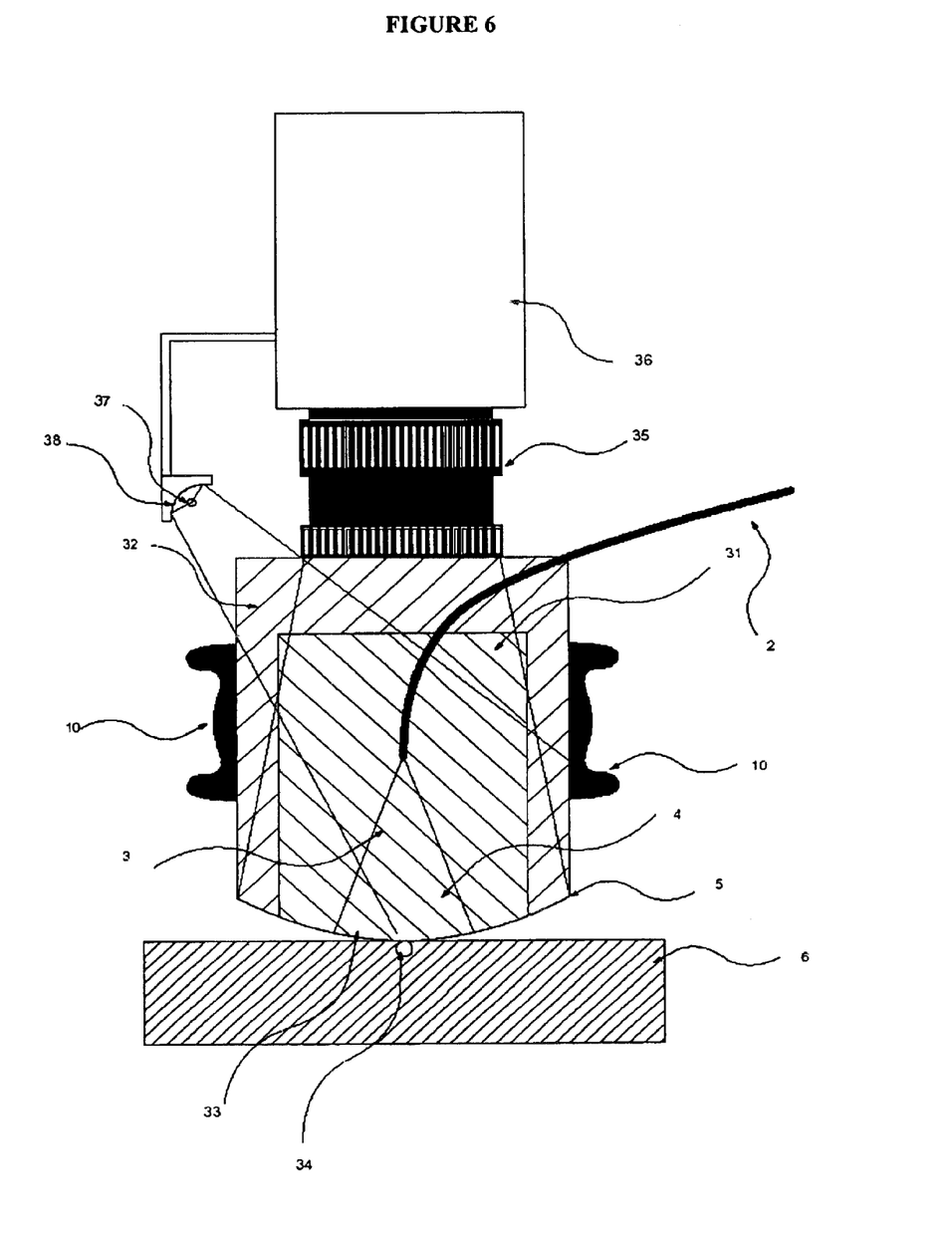
FIG. 6 shows an alternative embodiment of the handpiece and additional features.

FIG. 6 illustrates an embodiment of the monolithic handpiece that includes a number of additional features which are preferable for certain applications. In this embodiment, the handpiece is composed of more than one material, hence the bulk is formed from all materials. This allows the user to utilize the features of more than one material at different places. Inner material 31 is, as before, transparent to the process beam radiation. Confinement layer 32 is strongly absorbing for said radiation, but transparent at other wavelengths. This can be achieved by doping the material with ions that have an absorption peak at a certain wavelength. For example, the Neodymium Ion strongly absorbs radiation at about 808 nm, but is near transparent at visible wavelengths. In another example, confinement layer 32 is made of a borosilica glass, which absorbs ultraviolet radiation, while inner material 31 is quartz, which is transparent at UV wavelengths.

Another feature illustrated in FIG. 6 is shaped form 33 of the bulk bottom, in particular a spherical or cylindrical shape 33. This shape is advantageous for a number of medical treatments. One such example is a blood vessel treatment, where blood vessel 34 is punctually pressed down by the cylindrical bottom surface of the monolithic handpiece on the treatment site 6. By this method one can position and irradiate a vessel accurately and while also pressing the blood out of the vessel.

Observation of the treatment sight in this embodiment is indirect. Telescope 35 upon which CCD Camera 36 is mounted is positioned on the monolithic block. The images generated by this camera can be viewed live on a simple and cost effective monitor. CCD Cameras or similar devices have the advantage that they can detect wavelengths outside the visible range and are commercially available at low prices.

Additional viewing means could also include an optical system placed in the line of sight of the user suitable for magnifying the treatment site to facilitate accurate application of treatment or process radiation. This feature could also be used in conjunction with an aiming beam and/or reticule for further precision. Such an optical system could include a simple lens attached to the monolithic block or an attachment featuring interchangeable lenses or a zoom lenses for varying magnifications.

For special situations extra light source 37 can be mounted to the system. Its radiation is reflected via a mirror onto the treatment site. This illuminates the treatment sight in order to obtain better visibility. It can further be used in conjunction with medical treatment methods, for example to utilize fluorescence effects for diagnosis or to determine the accurate position of the treatment site.

All features of the described embodiments are not restricted to the special examples they are included in. More combinations are possible to obtain a tailored handpiece for a special application. It is to be understood that modifications to these examples by those skilled in the art may be effected within the scope and spirit of the invention as defined in the appended claims.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A laser safe treatment system consisting of a handpiece for topical application of electromagnetic radiation having protection from said radiation comprising:

a solid monolithic block, wherein said monolithic block is transparent to visible radiation and to process radiation;

at least one electromagnetic radiation source optically connected to said monolithic block, wherein said process radiation is at least partially propogated through said block;

a blocking means for preventing a process wavelength from freely exiting through exterior surfaces of said monolithic block that are not directed to a treatment site, wherein said blocking means is transparent to visible light other than the process wavelength; and wherein said handpiece provides a direct view of said treatment site through said handpiece during treatment.

2. A laser safe treatment system according to claim 1, further comprising means for maneuvering said monolithic block wherein said means for maneuvering allows a user an unfettered view of said treatment site.

3. A laser safe treatment system according to claim 1, wherein said blocking means is a suitable semitransparent coating able to confine said electromagnetic radiation to an interior of said monolithic block.

4. A laser safe treatment system according to claim 1, wherein said blocking means is a confinement layer comprising a material located within said monolithic block.

5. A laser safe treatment system according to claim 1, wherein said blocking means is selected from a group consisting of an absorbing material that absorbs said process wavelength, a reflecting material that reflects said process wavelength and a combination of said absorbing material and said reflecting material.

6. A laser safe treatment system according to claim 1, further comprising an aiming beam with a wavelength different from said process wavelength simultaneously coupled with said radiation source so that an optical path of said aiming beam through said handpiece coincides with an optical path of said process radiation.

7. A laser safe treatment system according to claim 1, wherein said monolithic block is made from a material selected from a group consisting of glass and fused silica.

8. A laser safe treatment system according to claim 1, wherein said monolithic block is made from a block of a transparent polymer.

9. A laser safe treatment system according to claim 1, wherein said radiation source is optically connected to means for coupling said radiation with said monolithic block so that said radiation source may be exchanged with a different radiation source.

10. A laser safe treatment system according to claim 1, further comprising means to prevent process radiation from entering said monolithic block; wherein said means is selected from a group consisting of a switch to trigger said electromagnetic radiation source and a safety switch to block said electromagnetic radiation source.

11. A laser safe treatment system according to claim 1, further comprising a system of closed and partially leaking channels integrated into said monolithic block through which a fluid can be transported for cooling and heating purposes.

12. A laser safe treatment system according to claim 1, wherein said handpiece is provided with at least one interlock system comprising an electrical contact switch, wherein said switch is connected to said means to prevent process radiation from entering said monolithic block, and wherein further correct positioning of said block causes said switch to close and allow activation of said radiation source.

13. A laser safe treatment system according to claim 1, further comprising a motor bellow to isolate the treatment or process area optically and mechanically from an environment around said treatment site.

14. A laser safe treatment system according to claim 1, further comprising at least one electronic observation means.

15. A laser safe treatment system according to claim 14, wherein said electronic observation means comprises a CCD camera with a suitable optical imaging system and a means for displaying provided images, wherein said means for displaying are selected from a group consisting of a screen and a computer device.

16. A laser safe treatment system according to claim 1, further comprising at least one plate transparent to said process wavelength, wherein said plate is located at a face of said block that is directed to said treatment site that separates said treatment site from said handpiece.

17. A laser safe treatment system according to claim 16, wherein said plate contains fluid or gas channels.

18. A laser safe treatment system according to claim 1, further comprising at least one spacer to keep said handpiece at a predetermined distance from said treatment site.

19. A laser safe treatment system according to claim 18, wherein said spacer comprises a system of closed and partially leaking channels through which a fluid can be transported for cooling and heating purposes.

20. A laser safe treatment system according to claim 1, wherein a face of said block that is directed to said treatment site is formed as a geometric shape in order to assist the specific treatment or process.

21. A laser safe treatment system according to claim 1, where said view is enhanced by a suitable optical system.

22. A laser safe treatment system according to claim 21, wherein said optical system comprises a lensed shape viewing surface to magnify details of said treatment site.

23. A laser safe treatment system according to claim 21, wherein said optical system is selected from a group consisting of a detachable system, an interchangable system and a variable system.

24. A laser safe treatment system according to claim 23, wherein said variable system consists of a zoom lens configuration.

25. A laser safe treatment system according to claim 1, further comprising at least one means to form and direct said process radiation integrated within said monolithic block.

26. A laser safe treatment system according to claim 25, wherein said means to form and direct said process radiation is selected from a group consisting of a lens, a waveguide, an optical fiber integrated into said monolithic block, and an optical fiber bundle integrated into said monolithic block.

27. A laser safe treatment system according to claim 1, wherein said monolithic block contains a cavity wherein at least one means to form and direct said process radiation can be inserted.

28. A laser safe treatment system according to claim 27, further comprising at least one vacuum line for aspiration and evacuation services.

29. A laser safe treatment system according to claim 28, further comprising an o-ring for use in conjunction with said vacuum line to create a desired atmospheric pressure in said cavity.

30. A laser safe treatment system according to claim 27, further comprising at least one supply line through which secondary process materials and therapeutical substances can be dispersed.

* * * * *